United States Patent [19]

Muth et al.

[11] Patent Number: 5,358,677
[45] Date of Patent: Oct. 25, 1994

[54] METHODS OF FORMING BIOABSORBABLE OBJECTS FROM POLYVINYL ALCOHOL

[75] Inventors: Ross R. Muth, Brookfield; Nagabhushanam Totakura, Norwalk, both of Conn.; Keith D'Alessio, Warsaw, Ind.

[73] Assignee: United States Surgical Corporation, Norwalk, Conn.

[21] Appl. No.: 852,964

[22] Filed: Mar. 17, 1992

[51] Int. Cl.⁵ ............... B29B 11/12; B29C 43/14; B29C 43/56
[52] U.S. Cl. ...................... 264/87; 264/120; 264/126; 264/129; 264/185; 264/299; 264/547; 264/553
[58] Field of Search ........... 264/185, 211, 338, 129, 264/571, 87, 316, 299, 120, 123, 126, 553, 547

[56] References Cited

U.S. PATENT DOCUMENTS

| | | | |
|---|---|---|---|
| 2,072,302 | 3/1937 | Herrmann et al. | 606/230 |
| 2,138,751 | 11/1938 | Vohrer | 524/21 |
| 2,146,295 | 2/1939 | Hermann et al. | 264/185 |
| 2,239,718 | 4/1941 | Izard | 264/185 |
| 2,265,283 | 12/1941 | Hermann et al. | 264/185 |
| 3,607,812 | 9/1971 | Takigawa et al. | 264/185 |
| 3,858,379 | 1/1975 | Graves et al. | 53/25 |
| 3,882,196 | 5/1975 | Hanke | 260/895 |
| 3,922,432 | 11/1975 | Lindgren et al. | 428/342 |
| 3,960,150 | 6/1976 | Hussain et al. | 128/260 |
| 4,124,677 | 11/1978 | Saijo et al. | 264/289 |
| 4,372,311 | 2/1983 | Potts | 604/364 |
| 4,493,807 | 1/1985 | Vyvial et al. | 264/185 |
| 4,705,039 | 11/1987 | Sakaguchi et al. | 128/334 |
| 4,743,258 | 5/1988 | Ikada et al. | 623/1 |
| 4,857,069 | 8/1989 | Kira | 623/1 |
| 4,863,472 | 9/1989 | Tormala et al. | 623/16 |
| 4,871,410 | 10/1989 | Bonnebat et al. | 264/185 |
| 5,002,526 | 3/1991 | Herring | 604/11 |
| 5,137,969 | 8/1992 | Marten et al. | 264/185 |

FOREIGN PATENT DOCUMENTS

| | | |
|---|---|---|
| 0113638 | 7/1984 | European Pat. Off. . |
| 0332318 | 9/1989 | European Pat. Off. . |
| 737034 | 7/1943 | Fed. Rep. of Germany . |
| 884689 | 8/1943 | France . |
| 48-42950 | 12/1973 | Japan ............... 264/185 |
| 50-129647 | 10/1975 | Japan . |
| 3142475 | 12/1978 | Japan . |
| 61-014916 | 1/1986 | Japan . |
| 4301409 | 10/1992 | Japan . |
| 35121 | 3/1931 | Netherlands . |
| 8301193 | 4/1983 | PCT Int'l Appl. . |

OTHER PUBLICATIONS

Experimental Nonsuture Microvascular Anastomosis Using A Soluble PVA Tube And Plastic Adhesive, Yamaguchi et al., Journal of Microsurgery, Nov./Dec. 1979.
Elvanol Product Literature, DuPont Polymers, Dec. 1990.
Airvol Polyvinyl Alcohol Product Literature, Air Products and Chemcials Inc., 1991.
Kirk-Othmer Encyclopedia of Chemical Technology, vol. 23, pp. 848–864, John Wiley & Sons, 1983.

*Primary Examiner*—Jay H. Woo
*Assistant Examiner*—Duane S. Smith

[57] ABSTRACT

Method for forming polyvinyl alcohol (PVA) into surgical elements include forming a mixture of PVA and water into a film by vacuum pressing with a first force, heating, applying a second force two to two hundred times the firs force, drying the film to remove water to a content of less than about 10% by weight based on the weight of the film, and molding the film into a desired shape.

26 Claims, No Drawings

METHODS OF FORMING BIOABSORBABLE OBJECTS FROM POLYVINYL ALCOHOL

FIELD OF THE INVENTION

This invention relates to methods of preparing bioabsorbable objects. More particularly, this invention relates to methods of preparing medical devices or surgical elements from polyvinyl alcohol.

BACKGROUND OF THE INVENTION

Polyvinyl alcohol (PVA) is a polyhydroxy polymer and, consequently, a water-soluble synthetic resin having the general formula:

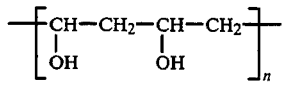

The largest application for PVA is in textile sizing. Other applications for PVA include its use in adhesives, paper coatings and as a polymerization aid. PVA has also been used as a component in soluble or bioabsorbable medical devices or surgical elements.

Various methods are described in the prior art for incorporating PVA into a medical device or forming such a device from PVA. For example, chemical attachment of a PVA coating to vascular protheses is described in U.S. Pat. No. 4,743,258.

Injection molding of PVA and modified PVA compounds has been suggested to form tampon applicators (U.S. Pat. No. 5,002,526) and components of bone graft implants (U.S. Pat. No. 4,863,472).

Solvent casting of PVA has been suggested for forming: a subsidiary device for suturing an intestine (U.S. Pat. No. 4,705,039); a bioerodible ocular device (U.S. Pat. No. 3,960,150); and a PVA-gel support pad from cross-linked PVA.

U.S. Pat. No. 3,922,434 describes a number of ways of applying a water soluble polymer such as PVA, to a paper substrate or carrier. One way of adding the polymer in connection with the manufacture of the carrier is to mix cellulose powder and pulverulent water soluble polymer, adding a small amount of water and then compression molding the mixture (See U.S. Pat. No. 3,922,434, column 4, lines 51-56).

PVA films oriented in two orthogonal directions may be produced in accordance with the methods described in U.S. Pat. No. 4,124,677.

The extrusion of a PVA rod which is chopped into pellets and then injection molded is described in U.S. Pat. No. 3,882,196.

In general, there are several problems associated with the molding of PVA. PVA is not easily molded as received from a supplier due to the fact that its melting temperature is above its degradation temperature. Therefore, a plasticizing agent, such as water, must be added. Only small amounts of water need to be added for the plasticizing effect to be experienced. However, adding only small amounts of water makes it very difficult to produce a homogenous mixture. A non-homogenous mixture results in an unacceptable product due to, among other things, non-uniform strength. Unfortunately, adding relatively large amounts of water causes the generation of numerous voids during the manufacture of a PVA film or object, again resulting in an unacceptable product.

Accordingly, it is an object of this invention to provide an improved method of forming soluble or bioerodible items from PVA.

It is a further object of the invention to provide a PVA molding process which overcomes the difficulties associated with known PVA molding techniques.

SUMMARY OF THE INVENTION

Bioabsorbable objects are produced in accordance with the present invention by preparing a mixture of polyvinyl alcohol and water and forming a film from the mixture by: i) applying a first, relatively low force to the mixture; ii) heating the mixture to a temperature of at least about 100° C. but below the degradation temperature of the polyvinyl alcohol; and iii) applying a second, relatively high force to the heated mixture. Water is then removed from the film and the film is molded into a predetermined form.

In another aspect, the present invention involves forming a mixture of PVA and water by adding water to PVA in small increments until the PVA/water mixture contains from about 15% to about 50% water by weight of the mixture. This mixture is then formed into a film. Water is removed from the film. The dried film is then molded into a desired shape.

DESCRIPTION OF THE PREFERRED EMBODIMENTS

Polyvinyl alcohol suitable for use in the present invention may be of any molecular weight. Preferably, medium to high molecular weight PVA is used. More preferably, PVA having a molecular weight of 78,000 to 80,000 may be utilized. Additionally, the level of hydrolysis of the PVA is not narrowly critical. A preferred hydrolysis level for the PVA is about 88 percent. It should be understood, of course, that various combinations of molecular weight and hydrolysis may be used to produce a product having a desired combination of physical properties. Suitable PVA is available under the tradename ELVANOL from DuPont Polymers, Wilmington, Del. and under the tradename AIRVOL from Air Products and Chemicals, Inc., Calvert City, Ky.

The first step in the methods of the present invention is forming a mixture of PVA and water. Preferably, the PVA/water mixture will contain from about 15% to about 50% by weight of water. Most preferably, the mixture will contain from about 25% to about 35% water.

The water may be added in any known manner. Preferably, the water is added in small increments while stirring the PVA vigorously. This will provide a substantially homogenous mixture of PVA and water having a dough-like consistency.

Optionally, once the PVA/water mixture is formed, a portion of the water may be removed. This can be accomplished by subjecting the mixture to reduced pressure, with or without heating. If this drying step is employed, it is preferred that the water level in the mixture remain between about 10% and about 25% by weight of the mixture.

The mixture is then formed into a film. Any known method may be used to form the film. Preferably, the film is formed by: i) applying a first, relatively low pressure to the mixture; ii) heating the mixture to a temperature of at least about 100° C. but below the degradation temperature of the PVA; and iii) applying a second, relatively high force to the heated mixture. The first, relatively low force may range from about 250 pounds to about 5000 pounds. Preferably the first, relatively low force is between about 500 and about 1500 pounds. The second, relatively high force applied to the mixture may range from about 10,000 pounds to about 50,000 pounds. Preferably, the relatively high force is between about 25,000 and 35,000 pounds. The second relatively high force is applied to the mixture once it has been heated to a temperature between 100° C. and degradation temperature of the plasticized PVA. The second force is preferably applied to the mixture at a temperature between about 130° and 190° C. The high pressure is maintained for a period of about 0.5 to about 30 minutes and is preferably maintained on the mixture during the cool down period. Cool down may be accomplished by any known technique, such as by spraying water mist or streaming water onto the press for anywhere from about 0.5 to about 30 minutes or longer.

In a particularly preferred embodiment the film is formed in a vacuum press. In this case, the chamber of the vacuum press may be evacuated to a pressure of about 1 to about 600 mm Hg, and preferably to a pressure of about 10 to 100 mm Hg.

Once the film is formed, water is removed from the film. The removal of water may be accomplished in any known manner. Preferably, the film is placed into a vacuum oven for a period of time. The parameters to which the vacuum oven is set may vary widely, but typically range from 1 to 600 mm Hg and 35° to 150° C. The duration of this drying step will vary depending upon the settings of the vacuum oven but may typically range from about 0.5 to as much as 24 hours or more. Preferably, water is removed from the film until water constitutes from about 2 to about 10% by weight of the film.

The next step in the methods of this invention is molding the film into a desired shape. Molding of the film into the final shape may be carried out in a vacuum press under conditions similar to those described above for forming the film.

Optionally, once the final product has been molded, water may be further removed by vacuum or otherwise to enhance the physical properties of the product, such as, for example to increase the stiffness of the product.

PVA-containing products prepared in accordance with this invention exhibit good strength, (typically having a strength between 15,000 and 40,000 psi) and rigidity (typically having a Young's modulus between 50,000 and 150,000 psi).

The following specific example is furnished in order to illustrate the invention. It constitutes exemplification only and is not to be regarded as a limitation.

EXAMPLE

A PVA/water mixture was prepared by placing 15 grams of 78,000 molecular weight PVA in a clean glass beaker and adding 7 grams of water heated to 45° C. in small increments while stirring vigorously. Vigorous stirring was continued for one minute after all the water had been added to ensure homogeneity of the mixture. The PVA/water mixture was kneaded into a small ball and placed in a vacuum chamber (0 to 25 mm Hg) at ambient temperature for about 2.5 hours.

The ball of resin was then placed into a vacuum press to form a PVA film. The chamber of the vacuum press was evacuated to 0 to 30 mm Hg and the heater was set to 175° C. After about six minutes, 1000 pounds of force was applied to the resin. When the temperature in the chamber reached 170° C., 30,000 pounds of force was applied to the resin. This condition (170° C., 30,000 lbs.) was maintained for five minutes. The press was cooled down while maintaining 30,000 pounds of force on the resin. Cool down included a water mist spray for six minutes followed by water for five additional minutes. The resulting PVA film removed from the press had a fairly uniform thickness of about 0.02 to 0.04 inches.

The film was then placed into a vacuum oven set at 60° C. and 0 to 25 mm Hg. After about eighteen hours in the vacuum oven, the film was removed and cut into strips approximately one-eighth of an inch in width. One strip was placed in each half of a suitable mold. The mold was closed and the loaded mold was placed into the vacuum press. The vacuum press was operated in the same manner described above to produce the PVA film. After cooling the molded PVA stent was removed and deflashed.

The resulting stents were two inches in length and 0.017 inches in diameter and suitable for insertion into the vas deferens in order to hold these tubular structures in close apposition during repair of the structures such as by suturing or application of laser energy. The stents should maintain their integrity for at least ten minutes and preferably will dissolve, disintegrate, lose strength and/or flow away in the system within three hours, advantageously holding the tubular structures in position for a sufficient time to allow repair, such as by suturing or laser welding. It should be understood that stents of other dimensions can be produced in accordance with the present invention for use with or insertion into other body tissue, Five samples prepared as described above were subjected to a three point bending test regime based on ASTM D790. The test span length was 0.336 inches and the crosshead speed was set at 0.5 inches per minute. The results are provided in Table I.

TABLE I

| Sample # | Max. Load (lbs.) | Max. Stress (psi) | Young's Modulus (psi) |
| --- | --- | --- | --- |
| 1 | 0.120 | 17,561 | 58,860 |
| 2 | 0.215 | 37,443 | 140,192 |
| 3 | 0.145 | 25,252 | 74,693 |
| 4 | 0.125 | 20,656 | 65,350 |
| 5 | 0.100 | 17,415 | 57,827 |
| Average | 0.141 | 23,665 | 79,384 |

Objects formed in accordance with this invention may consist essentially of PVA. Alternatively, other components may be added to provide a desired characteristic or function to the object. For example, plasticizers such as glycerol or polyethylene glycols may be added to make polyvinyl alcohol thermoplastic.

In addition, a coating of many types may be applied to the PVA object formed in accordance with this invention to alter the characteristics thereof. For example, a coating of a more slowly solubilized polymer may be applied to the PVA object to increase its resistance to hydrolytic attack. Suitable materials for a bioabsorbable coating include but are not limited to presently known synthetic or natural polymers which break down to non-toxic components when placed within a mammalian body, such as those identified in U.S. Pat. Nos. 4,719,917 and 4,916,193, which are incorporated herein by reference. For example, these include polyglycolide, polylactide, copolymers of glycolide and lactide, glycolide-trimethylene carbonate copolymer, mixtures of poly(glycolide-co-lactide) and polyethylene oxide, polydioxanone, polyesters formed from diols and succinic or oxalic acids, isomorphic copolyoxalates, poly(alkylene oxalates, polymalic acid, poly-beta-hydroxy acids, poly(hydroxyvalerates), poly(hydroxybuterates), polymers made from unsymmetrically-substituted 1,4-dioxane-2,5-diones, polycapralactone, copolymers of lactide or glycolide and epsilon cyprolactone, polyesteramides, partially oxidized cellulose surgical hemostats, chitin, chitin derivatives, collagen, regenerated collagen, catgut suture material, and mono-, di-, tri- and poly(saccharides). Preferred coating materials include polyglycolide, polylactide, copolymers of glycolide and lactide, and mixtures of polyglycolide-co-lactide and polyethylene oxide.

It should, of course be understood that the PVA may be molded into any desired shape. Typical objects which may be formed from PVA in accordance with the present invention for medical use include, but are not limited to Orthopedic pins, clamps, screws and plates, clips, staples, bone substitutes, stents, needles and vascular implants.

We claim:

1. A method of preparing a bioabsorbable object comprising:
   forming a mixture comprising polyvinyl alcohol and water, said mixture having a water content between about 25% and about 50% by weight water based upon the total weight of said mixture;
   drying the mixture to reduce the water content of the mixture to less than about 25% by weight based on the total weight of the mixture;
   forming a film from the mixture by pressing the mixture;
   drying said film until the water content of the film is no more than 10% based on the weight of the film; and
   molding the dried film into a shape.

2. A method as in claim 1 wherein said step of forming a film comprises:
   i) applying a first force to the mixture;
   ii) heating the mixture to a temperature of at least about 100° C. but below the degradation temperature of the polyvinyl alcohol; and
   iii) applying a second, force to the heated mixture, said second force being 2 to 200 times greater than said first force.

3. A method as in claim 2 wherein the mixture is heated to a temperature of about 130° to about 190° C.

4. A method as in claim 2 wherein said second force is about 16 to 70 times greater than said first force.

5. A method as in claim 1 wherein said molding step comprises:
   applying a first force to the film;
   heating the film to a temperature of at least about 100° C. but below the degradation temperature of the polyvinyl alcohol; and
   applying a second force to the heated film, said second force being 2 to 200 times greater than said first force.

6. A method as in claim 1 further comprising the step of removing water from the molded object.

7. A method as in claim 6 wherein said step of removing water from the molded object reduces the water content of the molded object to less than about 2% by weight based on the weight of the object.

8. A method as in claim 1 further comprising the step of applying a coating to the molded object.

9. A method as in claim 8 wherein said coating is selected from the group consisting of natural and synthetic bioabsorbable polymers.

10. A method as in claim 9 wherein said coating is selected from the group consisting of polyglycolide, polylactide, copolymers of glycolide and lactide, glycolide-trimethylene carbonate copolymer, mixtures of poly(glycolide-colactide) and polyethylene oxide, polydioxanone, polyesters formed from diols and succinic or oxalic acids, isomorphic copolyoxalates, poly-(alkylene oxalates, polymalic acid, poly-beta-hydroxy acids, poly(hydroxyvalerates), poly(hydroxybuterates), polymers made from unsymmetrically-substituted 1,4-dioxane-2,5-diones, polycapralactone, copolymers of lactide or glycolide and epsilon cyprolactone, polyesteramides, partially oxidized cellulose surgical hemostats, chitin, chitin derivatives, collagen, regenerated collagen, catgut suture material, and mono-, di-, tri- and poly(saccharides).

11. A method of preparing a bioabsorbable object comprising:
    placing a mixture comprising polyvinyl alcohol and water in a press;
    applying a first force to the mixture in the press;
    heating the mixture to a temperature of at least about 100° C. but below the degradation temperature of the polyvinyl alcohol;
    applying a second force to the mixture in the press, the second force being 2 to 200 times greater than the first force, such that a film of the mixture is formed;
    drying the film to remove water; and
    molding the film into a shape.

12. A method as in claim 11 wherein said step of removing water reduces the water content of the film to less than about 10% by weight based on the weight of the film 13. A method as in claim 11 wherein said mixture comprises between about 15% and about 50% by weight water based on the total weight of the mixture.

14. A method as in claim 11 wherein said molding step comprises:
    placing said film in a mold;
    placing the mold in a press;
    applying a first force to the mold;
    heating the mixture to a temperature of at least about 100° C. but below the degradation temperature of the polyvinyl alcohol;
    applying a second force to the mold, said second force being 2 to 200 times greater than said first force.

15. A method as in claim 11 wherein said second force is sufficient to form a film having a thickness of from 0.02 to 0.04 inches.

16. A method as in claim 11 wherein said second force is about 16 to 70 times greater than first force.

17. A method of preparing a bioabsorbable object comprising:
    placing a mixture comprising polyvinyl alcohol and water in a press;
    applying a first force to the mixture in the press;
    heating the mixture to a temperature of at least about 100° C. but below the degradation temperature of the polyvinyl alcohol;
    applying a second force to the mixture in the press, the second force being 2 to 200 times greater than the first force, such that a film of the mixture is formed;

drying the film to remove water and to reduce the water content of the film to less than about 10% by weight based on the weight of the film; and molding the film into a shape.

18. A method as in claim 17 wherein the mixture is heated to a temperature of about 130° to 190° C.

19. A method as in claim 17 wherein the water content is reduced to less than 2% by weight based on the weight of the film.

20. A method as in claim 17 further comprising the step of removing water from said mixture prior to forming a film therefrom.

21. A method as in claim 20 wherein the step of removing water from said mixture reduces the water content of said mixture to less than about 25% by weight based on the total weight of said mixture.

22. A method as in claim 17 further comprising the step of removing water from the molded object.

23. A method as in claim 22 wherein said step of removing water from said molded object reduces the water content of the molded object to less than about 2% by weight based on the weight of the object.

24. A method as in claim 17 wherein the polyvinyl alcohol has a high molecular weight.

25. A method as in claim 24 wherein the molecular weight of the polyvinyl alcohol is from about 78,000 to about 80,000.

26. A method as in claim 17 wherein said second force is about 16 to 70 times greater than said first force.

* * * * *